US007202352B2

(12) United States Patent
Katinger et al.

(10) Patent No.: US 7,202,352 B2
(45) Date of Patent: Apr. 10, 2007

(54) TUMOR AND SENESCENCE MARKER

(75) Inventors: Hermann Katinger, Vienna (AT); Johannes Grillari, Vienna (AT); Reingard Grabherr, Vienna (AT)

(73) Assignee: Polymun Scientific Immunbiologische Forschung GmbH, Vienna (AT)

( * ) Notice: Subject to any disclaimer, the term of this patent is extended or adjusted under 35 U.S.C. 154(b) by 525 days.

(21) Appl. No.: 10/181,059

(22) PCT Filed: Jan. 22, 2001

(86) PCT No.: PCT/EP01/00675

§ 371 (c)(1),
(2), (4) Date: Aug. 20, 2002

(87) PCT Pub. No.: WO01/53472

PCT Pub. Date: Jul. 26, 2001

(65) Prior Publication Data

US 2004/0086963 A1    May 6, 2004

Related U.S. Application Data

(60) Provisional application No. 60/177,216, filed on Jan. 12, 2000.

(51) Int. Cl.
*C07H 21/04* (2006.01)
*C07H 21/02* (2006.01)
*C12N 15/00* (2006.01)

(52) U.S. Cl. ..................... 536/23.1; 435/455
(58) Field of Classification Search ............... 530/350; 536/23.1; 435/455
See application file for complete search history.

(56) References Cited

U.S. PATENT DOCUMENTS

| 5,821,051 | A | * | 10/1998 | Androphy et al. | ............ 435/5 |
| 5,959,097 | A | * | 9/1999 | Monia et al. | ............ 536/24.5 |
| 6,020,136 | A | * | 2/2000 | Eberwine | .............. 435/6 |

FOREIGN PATENT DOCUMENTS

| WO | WO 97/41242 | 11/1997 |
| WO | WO 98/09643 | 3/1998 |
| WO | WO 99/07893 | 2/1999 |
| WO | WO 99/55858 A1 | 11/1999 |
| WO | WO 01/05970 A1 | 1/2001 |

OTHER PUBLICATIONS

Gotzmann et al. GenBank accession No. AJ1311 86, direct submission, submitted Nov. 27, 1998.*
Smith et al. The challenges of genome sequence annotation of "The devil in details" Nature Biotechnology (1997) vol. 15, pp. 1222-1223.*
Bork, P. Powers and pitfalls in sequence analysis: the 70% hurdle. Genome Research (2000) vol. 10, pp. 398-400.*
Gerner et al. Reassembling proteins and chaperones in human nuclear matrix protein fractions. Journal of Cellular Biochemistry (1999) vol. 74, pp. 145-151.*
R. Strausberg, *Nuclear Matrix Protein N:P200 Related to Splicing Factor PRP19*, EMBL Database, Jun. 2001, XP002172335.
F. Tashiro, et al., *Neuronal Differentiation-Related Gene*, EMBL Database, Oct. 2001, XP002172336.
J. Gotzmann, et al., *Identification of a Novel Nuclear Matrix Protein Related to Splicing Factor PRP19*, EMBL Database, May 2001, XP002172337.
A. Macieira-Coelho, *Markers of "Cell Senescence"*, Mechanisms of Ageing and Development, vol. 103, Jun. 1998, pp. 105-109, XP000990031.
C. Wistrom, et al., *Cloning and Expression of SAG: A Novel Marker of Cellular Senescence*, Experimental Cell Research, vol. 199, 1992, pp. 355-362, XP000990098.
Jacobs, et al., *The Oncogene and Polycomb—Group Gene bmi-1 Regulates Cell Proliferation and Senescence Through the ink4a Locus*, Nature, vol. 397, No. 6715, 1999, pp. 164-168, XP002144717.
O. Hohenwarter et al., *Stability of von Willebrand Factor Secretion in Different Human Endothelial Hybrid Cell Lines*, Cytotechnology, vol. 8, 1992, p. 31-37.
Goberdhan P. Dimri et al., *A Biomarker That Identifies Senescent Human Cells in Culture and in Aging Skin In Vivo*, Proceedings of the National Academy of Sciences, USA, Sep. 1995, p. 9363-9367.
Alex Bateman et al., *The Pfam Protein Families Database*, Nucleic Acids Research, vol. 28, 2000, p. 263-266.
Volker Brendel et al., *Methods and Algorithms for Statistical Analysis of Protein Sequences*, Proceedings of the National Academy of Sciences, Mar. 1992, p. 2002-2006.
Andrei Lupas, *Predicting Coiled-Coil Regions in Proteins*, Current Opinion in Structural Biology, vol. 7, 1997, p. 388-393.
Loesje van der Voorn et al., *The WD-40 Repeat*, Federation of European Biochemical Societies, Jul. 1992, p. 131-134.
Stephen F. Altschul et al., *Gapped BLAST and PSI-BLAST: A New Generation of Protein Database Search Programs*, Nucleic Acids Research, vol. 25, 1997, p. 3389-3402.
Jorg Schultz et al., *SMART: A Web-Based Tool for the Study of Genetically Mobile Domains*, Nucleic Acids Research, vol. 28, 2000, p. 231-234.

* cited by examiner

*Primary Examiner*—Celine Qian
*Assistant Examiner*—Tara L. Garvey
(74) *Attorney, Agent, or Firm*—Oliff & Berridge, PLC

(57) ABSTRACT

The present invention relates to cell-regulatory proteins and to nucleotide sequences encoding said proteins wherein the proteins have been found to be potential tumor and/or senescense markers useful for medical diagnostics and additionally having therapeutical potential as well as antiapoptotic properties useful for improving cell viability in cell culture technology. The invention further relates to antibodies directed against the cell-regulatory proteins and to their use in medical diagnostics and therapy. The invention further relates to methods for the manufacture and application of the cell-regulatory proteins and of the corresponding nucleotide sequences.

4 Claims, 4 Drawing Sheets

TUMOR AND SENESCENCE MARKER

This application is the U.S. National Stage of International Application No. PCT/EP01/00675, filed Jan. 22, 2001. This application claims the benefit of U.S. Provisional Application No. 60/177,216, filed Jan. 21, 2000.

TECHNICAL FIELD

The present invention is in the fields of biotechnology and medicine and relates to a protein that has been found to be a potential tumor and/or senescense marker useful for medical diagnostics and additionally having therapeutical potential as well as antiapoptotic properties useful for improving cell viability in cell culture technology.

INTRODUCTION

Serial passaging of human cells is a widely used model to study changes that occur during the process of aging on cellular level. Thereby important insights can be gained about the regulation of the cell cycle and the phenotype of cellular senescence.

Prior art cell fusion studies were able to demonstrate that the senescent phenotype is dominant over the transformed, immortal phenotype. Additionally, microinjection of mRNA derived from senescent cells induces the senescent phenotype in young cells, and inhibition of DNA synthesis is effected by a plasma membrane preparation of senescent and quiescent cells. This growth arrest occurs in the late G1 phase of the cell cycle and cells are blocked from entering S-phase, even if stimulated by any known combination of mitogens, although the growth factor receptors are still present on the cell surface. This irreversible growth arrest is dependent on the loss of telomerase activity, since fibroblasts transfected with the catalytical subunit hTERT do not enter replicative senescence, nor do they show tumorigenic alterations.

Reports about the gene expression during senescence locate changes in different groups of genes: cell cycle regulatory genes, transcription factors and growth factor inducible genes, extracellular matrix and secretory proteins, and mitochondrial genes.

BRIEF DESCRIPTION OF THE INVENTION

The present invention relates to the isolation and reproduction by recombinant genetic engineering techniques of nucleic acid sequences that encode a human protein (hereinafter called "SNEV proteins") or homologues thereof, which protein was found to interfere with cell regulatory processes that determine or affect at least one parameter selected from the group consisting of growth, viability, life span, and number of replication cycles, of a eukaryotic, e.g. a mammalian animal or human cell.

The invention further relates to the cell-regulatory SNEV protein itself as well as to its homologues and parts, e.g., functional domains, thereof. It also relates to the corresponding nucleotide sequences encoding the present proteins, homologues and parts, e.g. functional domains, thereof, as well as to the corresponding sense messenger RNAs (sense mRNAs) that translate into any one of the present proteins and peptides, and to antisense RNAs or PNAs that inhibit or prevent translation of the sense mRNAs.

The invention further relates to antibodies that are reactive with the present cell-regulatory SNEV proteins, homologues or parts thereof.

The invention also relates to the use of the present SNEV proteins, peptides, antibodies, nucleic acid sequences, sense mRNAS and antisense RNAs or PNAs in at least one field of application selected from the group consisting of diagnostics, medical therapy and cell culture technology, particularly for use in tumor, cancer and senescence diagnostics, prevention or therapy. In a specific embodiment, the invention relates to the use of the present SNEV proteins or corresponding nucleic acids for prolonging the lifespan of a eukaryotic cell in a suitable cell culture medium in vitro. In yet another specific embodiment, the invention relates to the opposite, i.e. to a wilful induction of a proliferation stop (senescence) of eukaryotic cells by decreasing intracellular levels of the SNEV protein using antisense RNA or anti-SNEV antibodies.

DETAILED DESCRIPTION OF THE INVENTION

Based on the knowledge of the aforementioned studies, a subtractive hybridization method was performed in order to isolate new senescence and/or growth regulatory genes, that might also be related to age associated diseases and tumorigenesis. For this purpose, one of the candidate genes was caused to be either recombinantly overexpressed or inhibited in HUVECs in order to clarify its biological significance.

By a subtractive hybridization method various differentially expressed genes were identified from early passage (5 P i.e. 5 passages) and senescent (35 P) human umbilical vein endothelial cells HUVECs and a previously unknown gene was identified, which is expressed at higher levels in young and quiescent than in senescent endothelial cells. From open reading frame analysis of the full length cDNA, an amino acid sequence was deduced, and the putative protein (hereinafter referred to as "SNEV" protein) represents a new member of the WD-repeat protein family. Transcription of this gene (hereinafter referred to as the "SNEV" gene) is not limited to endothelial cell lines, but was observed in all human tissues that we tested including kidney, lung, placenta, small intestine, liver, peripheral blood leukocytes, spleen, thymus, colon, skeletal muscle, heart, and brain. Moreover; no alternative splicing products have been identified so far. Additionally, homologous transcripts of the same length (2.3 kb) have been identified by Northern blots in CHO cells, in rat pituitary tissue and in a mouse tumour cell line, indicating that rodents express a conserved version of this mRNA.

This ubiquitous expression of SNEV suggests an important cellular function. Since we found this mRNA to be more abundantly expressed in early passage HUVECs than in their senescent counterparts, we determined corresponding expression levels in other cell lines. The results confirmed that the phenomenon of decreased SNEV mRNA levels in senescent cells is not limited to HUVECs, but can as well be seen in human diploid fibroblasts and in human kidney cells. Furthermore we were able to demonstrate that the decrease of SNEV mRNA is not a consequence of growth arrest but of senescence, since no different levels of SNEV between contact-inhibited HUVECs and cycling cells could be detected.

In contrast to the decreased transcription levels in senescent cells of e.g. endothelial, fibroblast, kidney or keratinocyte origin, SNEV mRNA levels have been found to be dramatically augmented in four different human leukaemia cell lines as compared to their normal controls, i.e. activated lymphocytes, as well as in a transformed keratinocyte cell line, and in SV40 transformed cells and kidney carcinoma cells, as compared to primary human kidney cells. Yet, two of the kidney carcinoma cell lines tested did not show extremely high levels of SNEV expression, however.

Various experiments revealed that overexpression of recombinant SNEV in HUVECs resulted in expansion of life span, whereas downregulation by antisense RNA transfection induced cellular senescence. These results underline the biological importance of the newly identified SNEV gene for controlling cell viability, senescence and immortalization of cell lines, and they are an additional indication for the close relationship between the irreversible proliferation stop (e.g. senescence) and tumorigenesis. The idea that replicative senescence might be a tumor suppressive mechanism was already contemplated in 1986 by O'Brien et al., Proc. Natl. Acad. Sci. USA 83, 8659–8663, and consistently ever since confirmed by various scientific evidence indicating that senescence and tumorigenesis are "opposite" cellular states.

In medical or biotechnologial practice, the SNEV gene, the SNEV protein and their homologues allow for purposively interfering with and modulating cell life span, including artificially accelerating cellular senescence on one hand, and prolonging cell life or even immortalizing cell lines on the other hand. Accordingly, they provide a promising basis for the development of useful diagnostic tools as well as for the development of pharmaceutical or other compositions for anti-tumor or anti-aging applications, particularly in the fields of medicine and cell biology as well as cell culture technology such as mammalian and plant cell culture technology.

Determining cellular levels of SNEV protein or SNEV mRNA will give the practitioner valuable information on the age status and on the likelihood of tumorigenic development of a cell or tissue of the human or animal body. Additionally; supplementing cells or tissues with SNEV protein, or in the alternative, upregulating SNEV expression by transfection of SNEV sense mRNA to such cells or tissues can interfere with apoptosis and prolong the lifespan of the cells or tissues, and perhaps even immortalize such cells or tissues. Moreover, transfecting antisense SNEV mRNA to target cells will reduce the transcription levels for SNEV ("downregulation") within these cells and thus force these cells, e.g. cells with high level expression of SNEV, such as tumor cells, into early senescense.

Homology search in the non redundant (nr) blast data base, identified only one match, a PAC clone which contains the chromosomal gene sequence of SNEV. In contrast, in the EST data base, about 100 clones derived from libraries of different tissues match our sequence. Several hundred base pairs of these clones had been sequenced from the 3'-end but no biological function was deduced from these data in the prior art.

From sequence analysis of the open reading frame an amino acid sequence was predicted and a homology search revealed 50% identity to a putative protein from the nematode *Caenorhabditis elegans* of 509 aa length, 41% to a putative protein from *Arabidopsis thaliana* of 540 aa, 30% to a hypothetical β-transducin from *Schizosaccharomyces pombe* and 24% to the pre-mRNA splicing factor PRP19 from *Saccharomyces cerevisiae*.

Cloning and sequence analysis of SNEV/mSNEV revealed five putative domains (FIG. 6, FIG. 7). Within the first 90 aa a U-box (a modified RING finger) domain was found by SMART search. This conserved domain is found in a large variety of proteins and possibly mediates the interaction of the U-box protein with ubiquitin conjugated proteins thus activating their further multi-ubiquitination. The NO terminal portion of SNEV was found to contain 7 WD-40 repeats that are similar to Gβ-like proteins. WD-40 repeats have a typical length of about 40 residues and form a β-propeller structure. WD-40 repeats are proposed to mediate protein-protein interactions (van der Voorn and Ploegh, 1992, FEBS Lett 307, 131–4), maybe with proline-rich regions. They are only found in eukaryotic organisms and regulate a large variety of cellular functions, such as cell division, cell differentiation, gene transcription transmembrane signaling, mRNA modification and vesicle fusion (Neer et al., 1994, Nature 371, 297–300). The putative coiled coil region represents another segment with protein-protein interaction ability.

The terms "homology", "homologous" or "homologues" as used herein shall be understood as to relate to a comparison of either two or more nucleic acid sequences or to a comparison of two or more amino acid sequences. The nucleic acid sequences may be full length DNA or RNA sequences such as entire genes or messenger RNA (mRNA) sequences, or parts thereof such as coding or non-coding regions, conservative regions, particularly interesting regions and the like, or any part of a nucleic acid sequence that is being compared with another nucleic acid sequence. Usually, a homology comparison is drawn from a nucleotide sequence produced or isolated according to the present invention to a nucleotide sequence that is known in the art, most frequently a naturally occurring nucleotide sequence from a living cell or a virus. Unless otherwise defined herein, "homologous" nucleotide sequences or "homologues" shall further be understood to comprise identical sequences as well as nucleotide sequences coding for the same amino acid sequence but varying in their nucleotide composition due to the degeneracy of the genetic code. Where an isolated or putative nucleotide sequence acording to the present invention comprises homologous and non-homologous parts as compared to a naturally occurring or otherwise known nucleotide sequence, the degree of homology is either expressed in quantitative terms, i.e. percentage of identity, or depicted graphically by a comparative showing in a table or a figure.

As concerns amino acid sequences, the terms "homologous" or "homologues" shall be understood to refer to either structurally (most usually) or functionally identical parts, regions or functional domains of entire proteins, of protein subunits, of parts of proteins, or of peptides, as compared to an amino acid sequence isolated or manufactured according to the present invention. Where there is no identity but only similarity, the degree of structural homology is expressed in quantitatve terms, i.e. percentage of identity, or depicted graphically by a comparative showing in a table or a figure. Functional homologues are understood to comprise proteins that perform the same or essentially the same function as one of the present proteins or domains thereof with which they are compared, although they may differ in structure from each other to a certain extent. Usually, functionally homologues are structurally closely related with each other.

The term "interactive" as used herein shall be understood to refer to a functional relationship between a protein or part of a protein of the present invention and an effector or substrate molecule, e.g. another protein or peptide, which functional relationship has in effect that either or both of the interactive molecules undergo changes in their structure and/or function. Usually, the interaction is such that it causes a functional domain of one or both of the interactive molecules to become activated or augmented in its activity, or, vice versa, to get inhibited or blocked.

Right picture: β-galactosidase stained HUVECs infected with PLXSN/SNEV-sense construct at passage 23. Blue staining as marker for cellular senescence is seen in SNEV antisense RNA infected cells only.

Figure 6:
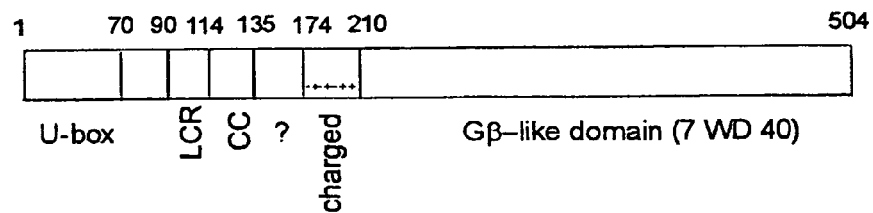

FIG. 6: Putative functional domains of SNEV.

Figure 7:
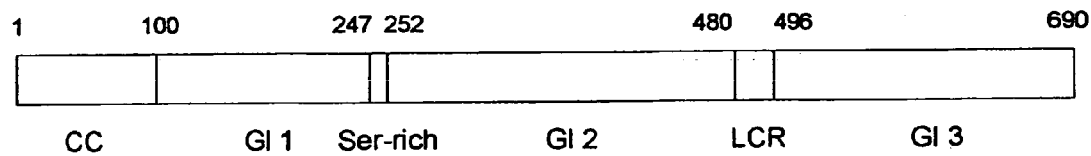

FIG. 7: Putative domains of SNEV: coiled coil (CC), globular domain 1 (Gl 1), globular domain 2 (Gl 2), serine-rich segment (Ser-rich), low complexity region (LCR), globular domain 3 (Gl 3).

Figure 8:
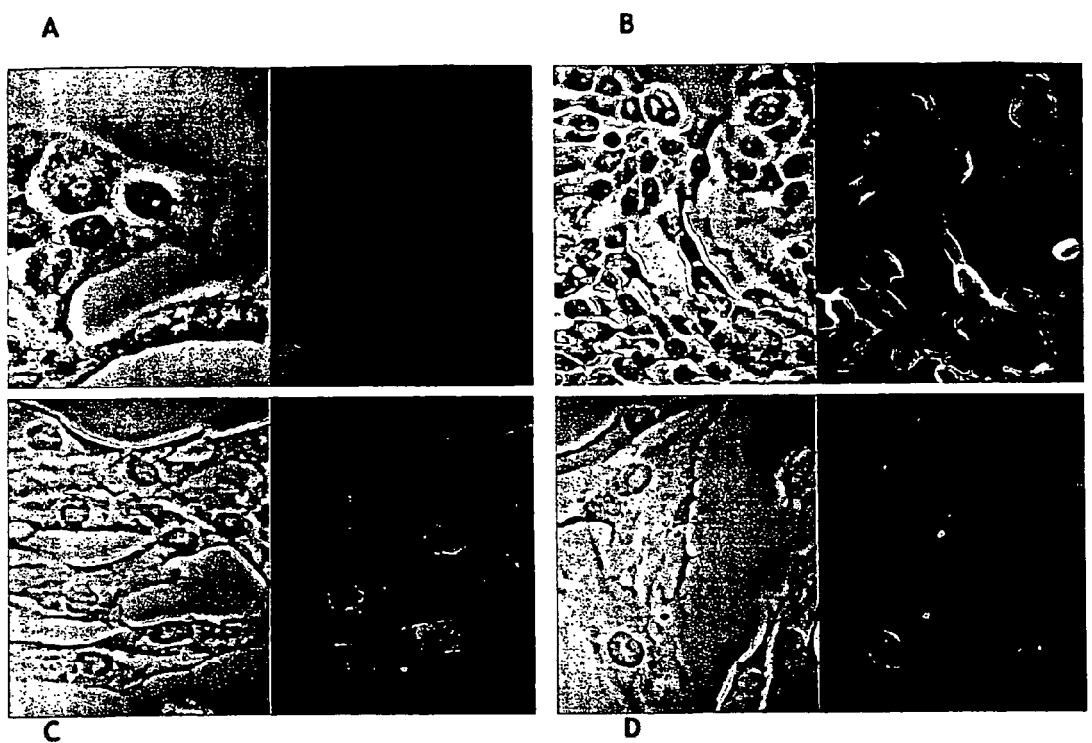

FIG. 8: Staining of SNEV in HaCat (A and B) and HDF (C and D) cells using indirect immunofluorescence. Pictures A through D show localization of SNEV inside the two cell lines.

Figure 9:
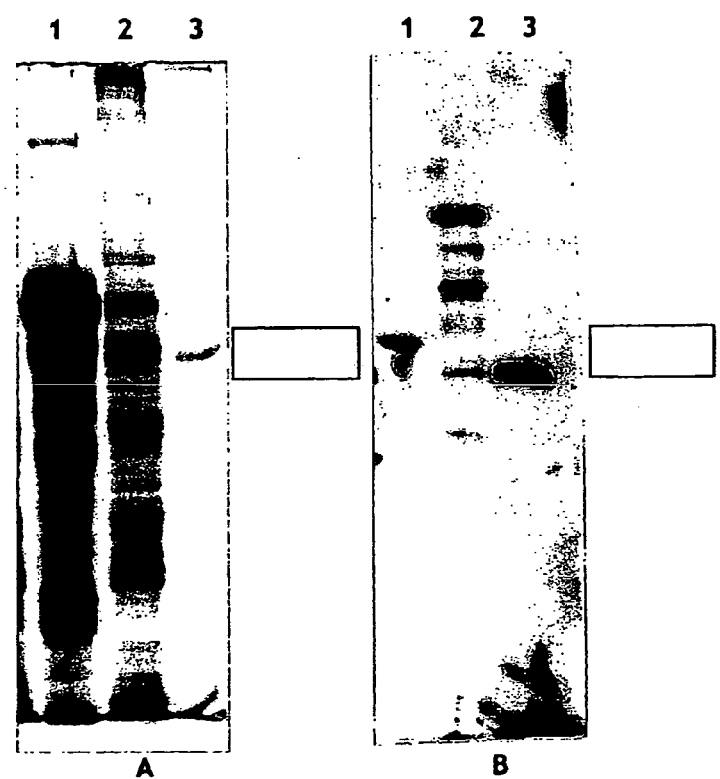

FIG. 9: Silver stained polyacrylamidgel (A) and Western blot (B) loaded with SNEV-transformed insect cell culture supernatant (lane 1), insect cell lysate (lane 2), and insect cell lysate after centrifugation (lane 3).

In order that the invention described herein may be more fully understood, the following examples are set forth. The examples are for illustrative purposes and are not to be construed as limiting this invention in any respect.

EXAMPLE 1

Preparation and Identification of SNEV Gene and Protein

Cell Culture:

Human umbilical vein endothelial cells (HUVECs) were isolated from umbilical veins and cultured as described in detail (Hohenwarter, et al., 1992, Cytotechnology 8, 31–37). Subsequently, cells were grown in gelatine-coated Roux bottles in M199 medium supplemented with 15% fetal calf serum (FCS), 200 µg/ml endothelial cell growth supplement and 90 µg 1 ml heparin in a humidified atmosphere containing 7% $CO_2$. Confluent cultures were detached by phosphate buffered saline (PBS) solution containing 0.1% trypsin and 0.01 EDTA and split in a ratio of 1:4 or 1:2. Early passage (young) cells were harvested after 5 passages, senescent cells (old) after reaching the irreversible growth arrest at 35 passages. Culture medium of HUVECs that were infected with the PLXSN/SNEV-sense and pLXSN/SNEV-antisense constructs contained 25 µg/ml G418 as selection pressure.

Fibroblasts were grown in DMEM/Ham's-F12 Medium (1:1) supplemented with 4 mM L-glutamine and 10% FCS. Young fibroblasts were harvested after 6 passages and senescent after 18 passages. Normal kidney cells (5 passages) and SV40 transformed (51 passages) kidney cells were kindly provided by R. Voglauer (IAM, Vienna, Austria). Senescent kidney cells were harvested after 17 passages. AA-2 (WIL-2 human splenic EBV+B lymphoblastoid cell line, National Institute of Allergy and Infectious diseases), MT-2 (human T-cell leukemia, National Institute of Allergy and Infectious Diseases Cat. Nr. 237), HL-60 (human promyelotic leukemia, ATCC) and Molt 3 (human acute lymphoblastic leukemia, T-cell, ATCC CRL 1552) were grown in Roux bottles with RPMI medium supplemented with 4 mM L-glutamine and 10% FCS. The cells were split in a ratio of 1:10.

A-498 (human kidney carcinoma, ATCC MTB 44) and HEK293 (human transformed embryonic kidney, ATCC CRL 1573) cell lines were grown in DMEM/Ham's medium supplemented with 4 mM L-glutamine and 10% FCS the medium of which contained only 5% FCS. Confluent cultures were detached by PBS solution containing 0.1% trypsin and 0.01 EDTA and split in a ratio of 1:10.

RNA Isolation:

Total RNA preparation using 1 ml TriZol (Life Technologies, USA) reagent/$5 \times 10^6$ cells was performed. Isolation of total RNA from HUVECs cell lines resulted in a mean yield of 33.53 µg total RNA/$10^6$ cells. mRNA was isolated using paramagnetic oligodT beads (Dynal, Norway).

Subtractive Suppression Hybridization:

Subtractive suppression hybridization was performed according to the manufacturer's protocol (Clontech, USA). Starting with 2 µg mRNA isolated from early passage (5 P.) and senescent (35 P.) HUVECs, subtractive PCR was used to create two cDNA pools, one enriched for genes accumulated in young cells, the other enriched for mRNAs accumulated in old cells.

These cDNA pools were ligated into pBlueskript KS II phagemid vector (Stratagene, USA), and electrocompetent *E. coli* TG 1 were transformed, creating the libraries Young-Old and Old-Young. Single colonies were picked and inserts were amplified by PCR using T3 and T7 primers (Stratagene, USA). Differential screening was performed by duplicate dot blots: 0.5 µl of each PCR-product were spotted onto two negatively charged nylon membranes (Amersham Pharmacia Biotech, Sweden), and immobilised by baking at 120° C. for 30 min. Complex probes were synthesised from the subtractive cDNA pools from Young-Old respectively Old-Young by Klenow enzyme and random hexanucleotide primers using a non-radioactive random labeling kit (Boehringer Mannheim, Germany). Hybridization with these DIG random labeled probes was carried out at 42° C. overnight in high SDS hybridization buffer (7% SDS, 50% formamide, 5×SSC, 2% blocking reagent, 50 mM sodium phosphate, pH 7.0, 0.1% N-lauroylsarcosine). The plasmids corresponding to cDNAs giving signals only with one complex probe were isolated by GFX micro plasmid prep kit (Amersham Pharmacia Biotech, Sweden) for further examination.

Northern Blots:

Candidate inserts were DIG-labeled using T3 and T7 primers together with the non-radioactive labeling kit (Boehringer Mannheim Germany) according to the manufacturer's protocol and then used as probes on Northern blots (Maniatis, et al., 1987) to confirm differential expression. 10 ng probe/ml high SDS hybridization buffer was used and hybridization was carried out overnight at 50° C. After stringent washing conditions, chemiluminescent signals were detected by autoradiography. The Northern blots contained 12 µg total RNA/lane and were run on 1%-denaturing agarose gels. To confirm that equal amounts of RNA were loaded onto the gel, blots were also hybridized to G3PDH.

Protein Sequence Analysis:

The protein sequences were tested for the occurrence of low complexity regions with the SEG program (Wootton and Federhen, 1996, Methods Enzymol 266, 554–71), coiled coil segments (Lupas, 1997, Curr Opin Struct Biol 7, 388–93), transmembrane regions (Claros and von Heijne, 1994, Comput Appl Biosci 10, 685–6), sequence compositional properties (Brendel et al., 1992, Proc Natl Acad Sci USA 89, 2002–6) and the occurrence of described globular domains from the PFAM (Bateman et al., 2000, Nucleic Acids Res 28, 263–6) and SMART (Schultz et al., 2000, Nucleic Acids Res 28, 231–4) databases. The existence of typical short structural repeats was also tested with the REP tool (Andrade et al., 2000, J Mol Biol 298, 521–37). The remaining suspected globular protein segments have been subjected to iterative databases with the BLAST/PSI-BLAST tool (Altschul et al., 1999, Nucleic Acids Res. 25, 3389–3402).

Sequence of mSNEV:

By sequencing the cDNA of mSNEV, which was reverse transcribed and amplified starting from a 3T3 mouse cell total RNA confirmed the EST-clone prediction. The sequence of mSNEV is shown in Table 1 below.

TABLE 1

Nucleotide sequence of mSNEV (SEQ ID NO 1), start and stop codons are pointed out by bold characters, a 5'-GC-rich homology region by italic characters.

AAGGCTGAGGCGCGCCACCGGCACCTCCCCACGTGAAGCAGAAGTGCGAG

CATCGCACGCTGGGCAGCTGTCTACCCGCGTCCGAGCGCT*CCGGAAGCGG*

*CGGGGGACCGGAAGTGGGCCGCGGAGGA*TGCAGAGAACCGGGAACCCTCT

GTGAGGCGACTGGCAGCAGGGCTACGACGGCGCCATGTCCCTGATCTGCT

CGATCTCCAATGAAGTGCCAGAGCACCCGTGCGTGTCCCTGTCTCTAAT

CATGTGTATGAGCGGCGACTCATTGAGAAGTACATTGCAGAGAATGGCAC

AGATCCTATCAACAACCAGCCTCTCTCAGAGGAGCAGGTCATCGACATCA

AAGTTGCTCACCCAATCCGACCCAAGCCTCCCTCCGCCACCAGCATCCCA

GCCATTCTGAAAGCCTTGCAGGATGAGTGGGATGCAGTCATGCTGCACAG

CTTCACTCTTCGCCAGCAACTGCAGACAACCCGCCAGGAGGTGTCCCATG

CTCTGTACCAACACGATGCTGCCTGCCGAGTCATTGCCCGGCTCACCAAA

GAGGTCACTGCTGCTCGAGAAGCTCTGGCTACTCTGAAACCACAGGCTGG

GCTTATTGTACCTCAGGCTGTGCCAAGCTCACAGCCCAGTGTTGTGGGTG

CAGGAGAGCCCATGGATTTGGGTGAGCTGGTGGGAATGACCCCTGAGATT

ATCCAGAAGCTTCAAGACAAGGCTACTGTGGTAACGACGGAGCGTAAGAA

GAGAGGAAAGACTGTCCCCGAGGAGCTGGTGAAACCTGAAGAGCTCAGCA

AGTACCGGCAGGTGGCATCCCATGTGGGTCTACACAGTGCTAGCATTCCT

GGGATTCTCGCTGTGGACCTGTGTCCCTCAGACACGAACAAGATTCTCAC

TGGTGGGGCAGATAAAAATGTTGTTGTCTTTGATAAGAGTACTGAGCAAA

TATTGGCCACTCTCAAAGGCCATACGAAGAAGGTCACCAGTGTGGTGTTT

CATCCTTCTCAGGAACTGGTGTTTTCTGCGTCCCTGATGCTACTATCAG

TABLE 1-continued

Nucleotide sequence of mSNEV (SEQ ID NO 1), start and stop codons are pointed out by bold characters, a 5'-GC-rich homology region by italic characters.

GATTTGGTCAGTCCGGAACACTTCCTGCGTACAGGTTGTTCGGGCCCATG

AGAGTGCAGTGACAGGCGTCAGCCTGCATGCTACTGGAGACTATCTCCTG

AGCTCCTCTGATGATCAGTACTGGGCCTTCTCTGACATCCAGACAGGGGG

TGTGCTCAGTAAGGTGACAGATGAGAGCTCCGGCTGCTCTCTTACCTGTG

CACAGTTCCACCCTGATGGGCTCATCTTTGGAACAGGAACCATGGACTCC

CAGATCAAGATCTGGGACTTGAAGGAGCGTACCAATGTGGCCAACTTCCC

TGGCCATTCTGGCCCCATTAGCAGCATCGGCTTCTCTGAGAATGGGTACT

ACCTGGCCACAGCAGCTGATGATTCCTCAGTCAAGCTCTGGGACTTACGC

AAGTTGAAGAACTTCAAGACATTGCAGCTGGACAACAACTTTGAGGTGAA

GTCACTAATCTTTGACCAGAGCGGTACGTACCTGGCGCTTGGGGGTACAG

ATGTCCAGATCTACATCTGCAAACAATGGACAGAGATTCTTCACTTTACA

GAGCACAGTGGCCTGACCACTGGAGTGGCCTTTGGACACCATGCCAAGTT

CATCGCTTCAACTGGCATGGACAGGAGCCTCAAATTCTACAGTCTGTAGG

CCCTATGCCTTCTCACAGTTCTGGGCCTCATCTCAGTAGTGGGTTAGAGT

TAGAGGGTGGGGGTGGGGGTGGGACTTTAGGAGGAGAGGGAGGTCTGGTT

GGGGGGGGACATTCACATGATTTCATTTTGGTCTGGATGATGGTCTGAGC

CAGGGCACATAGAACATTGCTATCCATGCAGCC

The putative coding sequence of mSNEV starts at bp 185 and stops at 1699, resulting in a protein of 504 amino acids (Table 2).

TABLE 2

Amino acid sequence of mSNEV (SEQ ID NO 2)
MSLICSISNEVPEHPCVSPVSNHVYERRLIEKYIAENGTDPINNQPLSEE

QLIDIKVAHPIRPKPPSATSIPAILKALQDEWDAVMLHSFTLRQQLQTTR

QELSHALYQHDAACRVIARLTKEVTAAREALATLKPQAGLIVPQAVPSSQ

PSVVGAGEPMDLGELVGMTPEIIQKLQDKATVLTTERKKRGKTVPEELVK

PEELSKYRQVASHVGLHSASIPGILALDLCPSDTNKILTGGADKNVVVFD

KSTEQILATLKGHTKKVTSVVFHPSQELVFSASPDATIRIWSVPNTSCVQ

VVRAHESAVTGLSLHATGDYLLSSSDDQYWAFSDIQTGRVLTKVTDETSG

CSLTCAQFHPDGLIFGTGTMDSQIKIWDLKERTNVANFPGHSGPITSIAF

SENGYYLATAADDSSVKLWDLRKLKNFKTLQLDNNFEVKSLIFDQSGTYL

ALGGTDVQIYICKQWTEILHFTEHSGLTTGVAFGHHAKFIASTGMDRSLK

FYSL

The homology of the coding sequence to human (90%) and rat (96%) sequences is very high. Interestingly, a second highly homologous region lies in the 5'-UTR 94 bp upstream of the start codon in mouse and human, and at −97 bp in rat.

This region is a GC-rich stretch of 39 bp (italic and underlined in Table 1) with only three bases difference between mouse and human, and only one between mouse and rat.

With sensitive sequence analysis methods, the following functionally different sequence segments of SNEV were detected (FIG. 6): a U-box domain hit from the SMART (1–70, E-value<$10^{-28}$; possible role in E2 dependent ubiquitination processes), a moderately polar low complexity region (91–101), a putative coiled coil segment (115–135), a highly charged region (10 positive, 6 negative out of 36 aa from 175–208), and a large Gβ-like domain containing 7 WD-40 repeats in accordance with PFAM, SMART and REP hits (210–504, E-values between $10^{-12}$ and $10^{-1}$). Yet another, probably globular domain (136–174) remains functionally uncharacterized.

Sequence database searches revealed close full-length sequential homologues in rat (Acc.No.: BAA95215), *D. melanogaster* (Acc.No.: AAD46846), *C. elegans* (Acc.No.: Q10051), *A. thaliana* (two different hits: Acc.No.: AAB80652 and Acc.No.: AAB70423), *P. falciparum* (Acc.No.: T18432), *S. pombe* (Acc.No.: O14011). The yeast PRP19 RNA splicing factor has similarity with SNEV over the ~130 N-terminal residues.

Full Length Transcripts:

After isolation of Rsa I digested gene fragments, it was necessary to isolate the corresponding full length transcripts. The Smart Kit (Clontech, USA) has been designed to specifically enrich full length cDNA based on the fact that the reverse transcriptase adds an oligo(dG) tail only when polymerisation of the DNA copy is complete. Specific primers were designed for selective amplification of full length cDNA. The reactions were performed according to the manufacturer's protocol. In brief, 1.0 µg of total RNA was reverse transcribed in a volume of 10 µl containing 10 pM of Smart oligonucleotide, 10 pM of CDS/3'-primer, 10 pM dNTPs, 20 pM DTT and 200 U Superscript II Reverse Transcriptase (Life Technologies, USA) in first strand buffer. Reverse transcription was carried out at 42° C. for one hour. PCR was performed on a Perkin Elmer (USA) 9600 Thermocycler in a volume of 100 µl containing 2 µl of the first strand reaction mix, 20 pM dNTPs, 20 pM of 5'-PCR primer, 20 pM CDS/3"-primer and 1×KlenTaq polymerase mix. After a denaturation step at 95° C./1 min, 25 cycles 95° C./15 sec 68° C./5 min were performed.

Sequencing analysis and comparison to Blast data base revealed that the gene fragment contained in clone 8/5–35 matched to portions of a chromosomal DNA sequence from human chromosome 11. These partial matches suggest the presence of several exons. Thus, chromosomal DNA from human PAC-clone pDJ606g6 was searched for exons and introns by exon finder programs (e.g., http://www-hgc.lbl.gov/inf/genie.html, http://CCR-081.mit.edu/GENSCAN.html, and http://grail.genome.ad.jp/Grail-1.3/) and mRNA sequence was predicted. Primers were designed to confirm the predicted coding sequence.

Full Length Transcript of SNEV:

The following nucleotide sequence was isolated with a primer pair lying outside the open reading frame of the first and last exon (Table 3).

TABLE 3

Nucleotide sequence of SNEV (SEQ ID NO 3)
CAGCAGCGGGGACCGGAAGTGGCTCGCGGAGGCTCAGAAGCTAGT

CGCGGAGCCCGGCGTGTGGCGCCTCGGAGCGCGGTGACGGCGCCATG

TCCCTAATCTGCTCCATCTCTAACGAAGTGCCGGAGCACCCATGTGTA

TCCCCTGTCTCTAATCATGTTTATGAGCGGCGGCTCATCGAGAAGTAC

ATTGGGGAGAATGGTACCGACCCCATCAACAACCAGCCTCTCTCCGA

GGAGGAGCTCATCGACATCAAAGTTGCTCACCCAATCCGGCCCAAGC

GTCCCTCAGCCACCAGCATCCCGGCCATTCTGAAAGCTTTGCAGGAT

GAGTGGGATGCAGTCATGCTGCACAGCTTCACTCTGCGCCAGCAGCT

GCAGACAACGCGCCAAGAGCTGTCACACGCTCTGTACCAGCACGATG

CCGCCTGCCGTGTCATTGCCCGTCTCACCAAGGAAGTCACTGCTGCCC

GAGAAGCTCTGGCTAGCCTGAAACCACAGGCTGGCCTCATTGTGCCC

CAGGCTGTGCCAAGTTCCCAACCAAGTGTTGTGGGTGCGGGTGAGCC

AATGGATTTGGGTGAGCTGGTGGGAATGACCCCAGAGATTATTCAGA

AGCTTCAAGACAAAGCGACTGTGCTAACCACGGAGCGCAAGAAGAG

AGGGAAGACTGTGCCTGAGGAGGTGGTGAAGCCAGAAGAGCTCAGC

AAATACCGGCAGGTGGCATCCCACGTGGGGTTGCACAGTGCCAGCAT

TCCTGGGATCCTGGCCCTGGACCTCTGCCCGTCCGACACCAACAAGA

TCCTCACTGGTGGGGCGGATAAAAATGTGGTTGTGTTTGACAAAAGTT

CTGAACAAATCCTGGCTACCCTCAAAGGCCATACCAAGAAGGTCACC

AGCGTGGTGTTTCACCCTTCCCAGGACCTGGTGTTTTCTGCTTCCCCC

GATGCCACTATCAGGATTTGGTCGGTCCCCAATGCCTCTTGTGTACAG

GTGGTTCGGGCCCATGAGAGTGCTGTGACAGGCCTCAGCCTTCATGC

CACTGGCGACTATCTCCTGAGCTCCTCCGATGATCAGTACTGGGCTTT

CTCTGACATCCAGACAGGGCGTGTGCTCACCAAGGTGACAGATGAGA

CCTCCGGCTGCTCTCTCACCTGTGCACAGTTCCACCCTGACGGACTCA

TCTTTGGAACAGGAACCATGGACTCTCAGATCAAGATCTGGGACTTG

AAGGAACGTAGTAATGTGGCCAACTTCCCTGGCCACTCGGGCCCCAT

CACTAGCATCGCCTTCTCTGAGAATGGTTACTACCTGGCTACAGCGGC

TGATGACTCCTCTGTCAAGCTCTGGGATCTGGGCAAGCTTAAGAACTT

TAAGACTTTGCAGCTGGATAACAACTTTGAGGTAAAGTCACTGATCTT

TGACCAGAGTGGTACCTACCTGGCTCTTGGGGGCACGGATGTCCAGA

TCTACATCTGCAAACAATGGAGGGAGATTCTTCACTTTACAGAGCATA

GCGGCCTGACCACAGGGGTGGCCTTCGGGCATCACGCCAAGTTCATC

GCTTCAACAGGCATGGACAGAAGCCTCAAGTTCTACAGCCTGTAGGC

CCTGGCCCTTCTGATGGAAGCTGGGGCTCATCTCAGTAGAGGGGTAG

AATTAGGGTTTGGGGGGGGGTGGGGGGAATCTATGGGGGAGGGG

GCTCTGTGGGTGGGACATTCACATCATTTCACTCTGGTCTGAGTGGT

GGCCTGAGAACCATGGTGGCATGGACCACCCTCATCCATGCAACTCC

AGGGCCCATGGGAACGGATGTGGAAGGAAGAACTGTCACCCTCTTAA

TABLE 3-continued

Nucleotide sequence of SNEV

GGCCCAGGGTCGGAGCCCAGGGCCTCTGCCTTCCTGTCGTTCAATGG

ACGTGGTGGTGGCTGTTCGAGACCCATTTTGTTGCAGTTCCTGTGAGA

CAGGAGAGGCTGAGCCAAGGGAACTGTGAAGGGGATGGGCAGGAGG

GCTTGTGCAGGGTTTTGTAAGCAGTGATCTAGTTTCATTAAAAAAAGA

AAACAATAACCATAACCAGCTCCCCGTGTCTGTCTGCACCAGGAGCA

CCTGGGACTGGGAAGGTCAAGGGGAGGGAGCACACACTGGGACACT

GGCTTCCGGGAAGCCCATCTTCCTTTCCTTTCACAGCTCTTACCCTTTT

TTTTTTTTTTTTAATTGCAGAGCAGAAATAAAAACAAATCTGC

Amino Acid Sequence of SNEV Protein:

This nucleotide sequence is translated into the following amino acid sequence (Table 4):

TABLE 4

Amino acid sequence of SNEV (SEQ ID NO 4)
MSLICSISNEVPEHPCVSPVSNHVYERRLIEKYIAENGTDPINNQPLSEE

QLIDIKVAHPIRPKPPSATSIPAILKALQDEWDAVMLHSFTLRQQLQTTR

QELSHALYQHDAACRVIARLTKEVTAAREALATLKPQAGLIVPQAVPSSQ

PSVVGAGEPMDLGELVGMTPEIIQKLQDKATVLTTERKKRGKTVPEELVK

PEELSKYRQVASHVGLHSASIPGILALDLCPSDTNKILTGGADKNVVVFD

KSSEQILATLKGHTKKVTSVVFHPSQDLVFSASPDATIRIWSVPNASCVQ

VVRAHESAVTGLSLHATGDYLLSSSDDQYWAFSDIQTGRVLTKVTDETSG

CSLTCAQFHPDGLIFGTGTMDSQIKIWDLKERTNVANFPGHSGPITSIAF

SENGYYLATAADDSSVKLWDLRKLKNFKTLQLDNNFEVKSLIFDQSGTYL

ALGGTDVQIYICKQWTEILHFTEHSGLTTGVAFGHHAKFIASTGMDRSLK

FYSL

In conclusion, the mRNA of the newly identified gene shows a length of 2251 bp, consistent with the transcript observed on Northern blots. The start codon is located at position 91, the stop codon at position 1603, and the poly-adenylation signal at 2200 (underlined bases in Table 3). Computational analysis of the chromosomal DNA segment 11p12.2 revealed 17 exons within 16 kb. The length of the exons ranges from 19 to 171 bp (see also the matching of SNEV to the chromosomal DNA). Translation of the mRNA resulted in a protein of 504 amino acids, whose putative cellular localisation is cytoplasmic or nuclear, as suggested by the PSORT program (http://psort.nibb.ac.jp:8800/) available via internet. This was confirmed by experimental identification of the protein as a nuclear matrix protein (Dr. Sauermann et al., Institute of Tumor Biology & Cancer Research, University of Vienna, Austria).

Hydrophobicity was calculated to be at −0.26 and a putative molecular weight of 55.2 kd was predicted. The molecular weight was confirmed by Western blot analysis (FIG. 9).

EXAMPLE 2

Expression of SNEV in Tissues and Cell Lines

Figure 1:
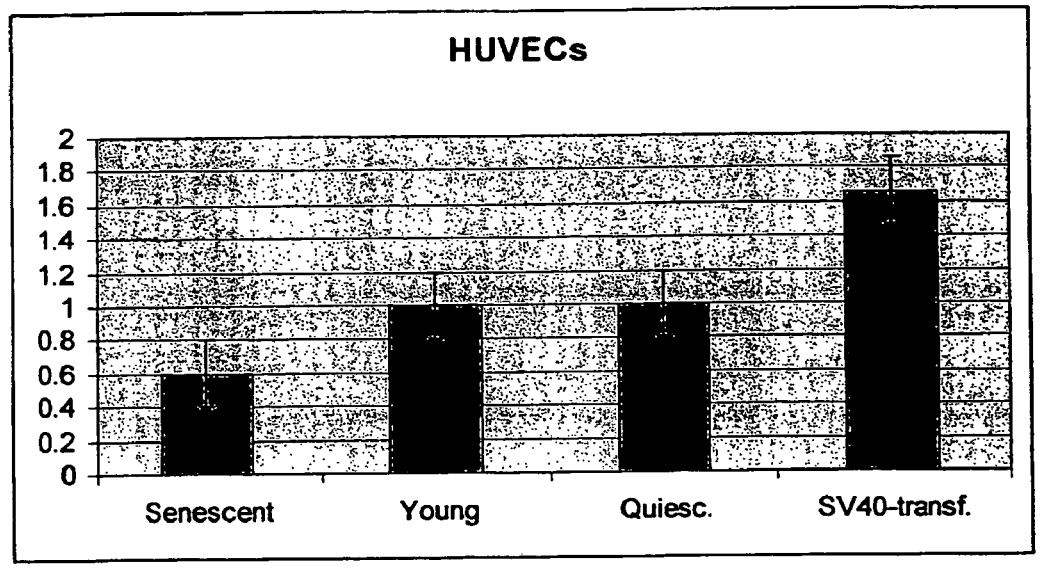
FIG. 1: relates to the expression of SNEV in HUVECs. The expression levels of SNEV are presented as multiples of the levels in young cells.

By using multiple tissue Northern blots (MTN) we found SNEV mRNA to be present in all human tissues represented on the blot: kidney, lung, placenta, small intestine, liver, peripheral blood leukocytes, spleen, thymus, colon, skeletal muscle, heart and brain. Additionally, there are homologues of the same length in rat, mouse and CHO cells (data riot shown). SNEV mRNA levels were quantified in different cell lines. In HUVECs, increased levels were observed in young cells, quiescent cells and SV40 transformed cells versus senescent cells (FIG. 1).

Figure 2:
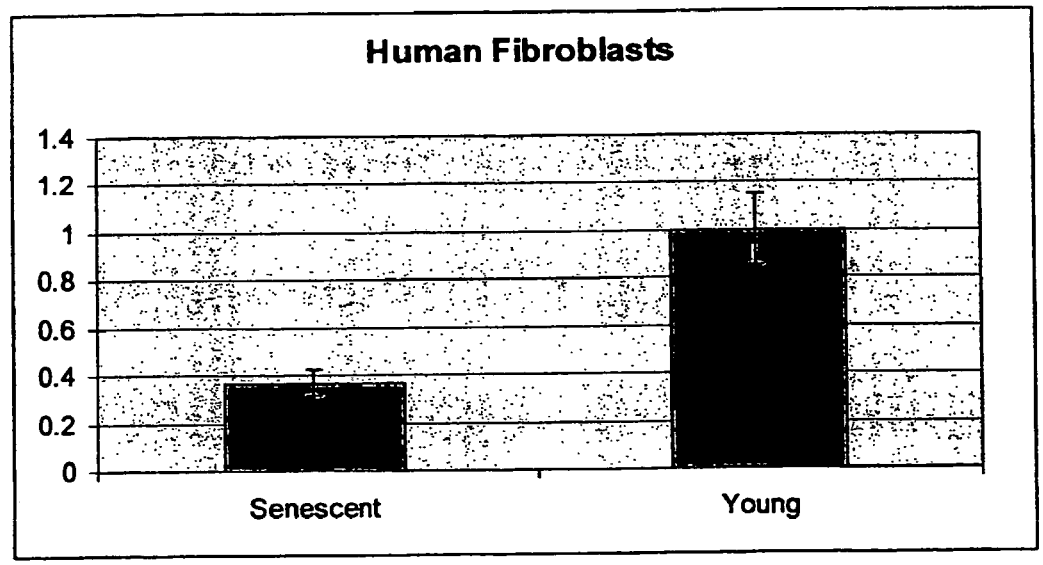
FIG. 2: relates to the expression of SNEV in human diploid fibroblasts. The expression levels of SNEV are presented as multiples of the levels in young cells.

Similarly, in human diploid fibroblasts derived from skin, SNEV mRNA was detected to be more abundantly transcribed in young cells (FIG. 2).

Figure 3:
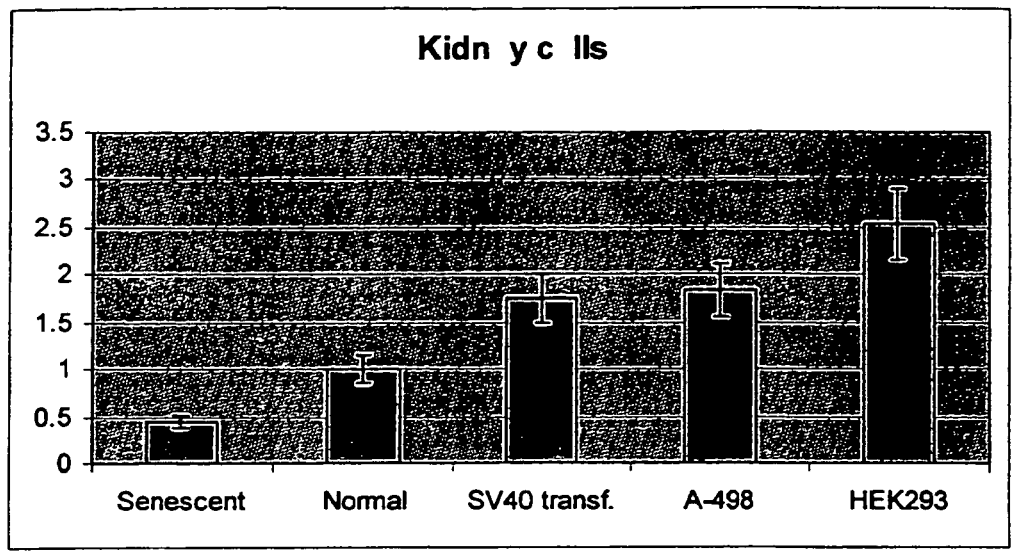
FIG. 3: relates to the expression of SNEV in kidney cells. The expression levels of SNEV are presented as multiples of the levels in normal kidney cells.
Figure 4:
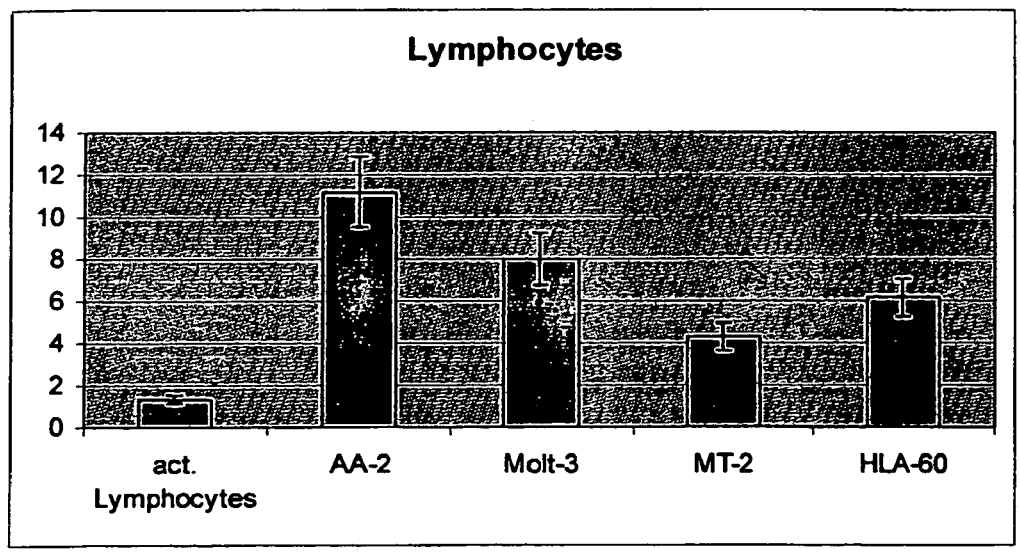
FIG. 4: relates to the expression of SNEV in lymphocytes. The expression levels of SNEV are presented as multiples of the levels in activated lymphocytes.

Based on the results from endothelial cells and fibroblasts it was assumed that mRNA levels not only decrease in senescent cells, but also rise in tumor cell lines. In order to test this hypothesis we compared the mRNA levels of different immortalized cell lines to their corresponding primary cell line. In kidney cells the difference between young and senescent cells was in accordance with the results derived from fibroblasts and HUVECs. The increase (FIG. 3) in SV40 transformed kidney cells and in immortalized cell lines was not as pronounced as in lymphocytes (FIG. 4), where an increase up to tenfold was detected. The difference of a normal keratinocyte cell line (3 passages) and the HaCat cell line could not be evaluated, since no signal could be detected in primary cells (data not shown).

EXAMPLE 3

Recombinant Expression of Sense and Antisense SNEV mRNA in HUVECs

Construction of Sense and Antisense Constructs:

Transfection of HUVECs with recombinant SNEV was performed using Clontech's retroviral gene transfer and expression kit according to the manufacturer's protocol. In brief, SNEV cDNA was amplified using the primers retro SNEV sense (5'-GAC GGT TAA CAT GTC CCT AAT CTG CTC CAT-3'; SEQ ID NO 8) and retro SNEV antisense (5'-GAC CGT TAA CCC TAA TTC TAC CCC TCT AC-3'; SEQ ID NO 9) and blunt end ligated into the retroviral plasmid pLXSN, creating the PLXSN/SNEV-sense and pLXSN/SNEV-antisense constructs. These constructs were transfected into the packaging cell line Retropack PT67 (Clontech, USA) by lipofection. Stably transfected cell lines were chosen and their culture supernatant was used to infect HUVECs at passage 14.

After transfection of HUVECs (passage 14) with SNEV antisense virus and selection of positive clones by G418 resistance, the cells expressing the SNEV antisense RNA under the constitutive SV40 promotor entered replicative senescence at passage 17. In contrast the cells expressing SNEV sense mRNA are at passage 23 and continue growth. Furthermore, faster growth of normal and sense transfected cells compared to antisense transfectants was observed. After transfection HUVECs were also cultivated without G418. When G418 was added to the cells after 4 passages, viable clones were obtained only for HUVECs transfected with SNEV sense mRNA.

Figure 5:
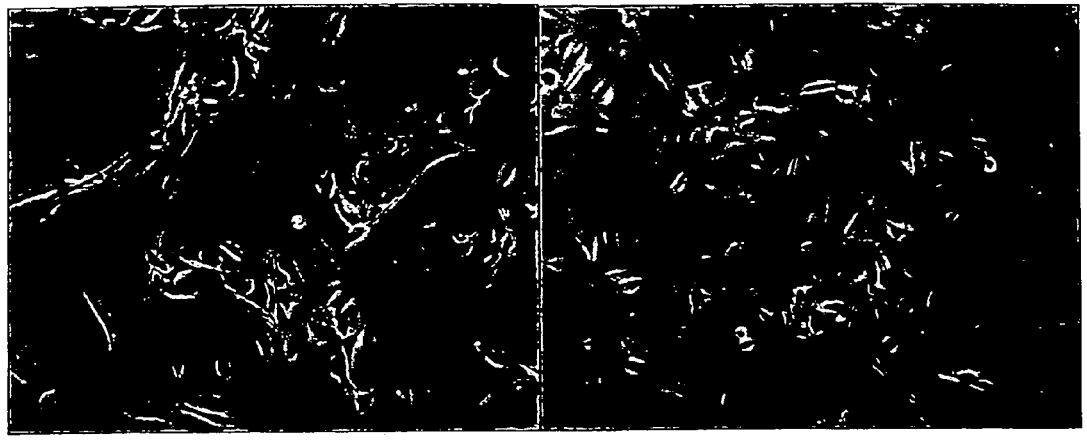
FIG. 5: Left picture: β-galactosidase stained HUVECs infected with pLXSN/SNEV-antisense construct after entering cellular senescence at passage 17.

The phenotype of the antisense transfected senescent cells was compared to that of normal senescent HUVECs and no morphological differences could be detected. Cellular senescence was also confirmed by senescence associated β-galactosidase staining (FIG. 5).

Staining of the Senescence Associated β-Galactosidase:

Staining of the senescence associated β-galactosidase was performed as described previously (Dimri, et al., 1995, Proc Natl Acad Sci USA 92, 9363-9367). After removal of the culture medium, the cells were washed twice with PBS and fixed with a fixing solution containing 2% formaldehyde and 0.2% glutaraldhyde in PBS. The cells were incubated for 5 min at room temperature and washed twice with PBS. Staining was carried out overnight at room temperature with a solution containing 1 mg/ml X-gal, 5 mM potassium ferricyanide, 5 mM potassium ferrocyanide, 2 mM MgCl2 in citric/phosphate buffer pH 6.0.

EXAMPLE 4

Controlling Life Span of Mammalian Cells by Application of SNEV mRNA

In order to shed more light on the biological role of SNEV in mammalian cells, HUVECs were transfected with a viral vector containing the sense mRNA of SNEV resulting in a corresponding overexpression of SNEV protein, and in a parallel experiment, with antisense RNA of SNEV resulting in a corresponding downregulation of SNEV protein. After downregulation of SNEV, HUVECs entered the state of cellular senescence 3 passages after transfection, whereas overexpression resulted in continued growth. The experimental data suggest a direct role of SNEV in the regulation of cellular proliferation and in replicative senescence. Instead of antisense RNA suitable PNAs (peptide nucleic acids) may also be used for performing antisense strategy in order to inhibit or prevent SNEV sense mRNA translation.

EXAMPLE 5

Cloning of the Mouse Homologue of SNEV Protein (=mSNEV)

Total RNA preparation from a mouse cell line 3T3 using 1 ml TriZol (Life Technologies, USA) reagent/$5 \times 10^6$ cells was performed. 1.0 µg of total RNA was reverse transcribed in a volume of 10 µl containing 10 pM Oligo($dT_{30}$) oligonucleotide, 10 pM dNTPs, 20 pM DTT and 200 U Superscript II Reverse Transcriptase (Life Technologies, USA), and 1×RT-buffer (Life Technologies, USA). Reverse tranorption was carried out at 42° C. for one hour. By comparison of the human sequence of SNEV to the mouse EST division of gene bank database (Altschul et al., 1999, Nucleic Acids Res. 25, 3389–3402) the consensus sequence of different EST-clones was determined as putative mSNEV sequence. Primers were designed (mSNEV sense: 5'-AAC CCT CTG TGA GGC GAC TG-3'; (SEQ ID NO 10; and mSNEV antisense: 5'-CCA CTA CTG AGA TGA GGC CC-3'; SEQ ID NO 11) in order to amplify the coding sequence and polymerase chain reaction (PCR) was performed in a buffer containing 20 pM of each primer, 0.1 µl of the RT-reaction as template. PCR cycles were 94° C./20 s, 55° C./30 s and 72° C./2 min. The PCR-product was cloned into pBlueskript KS II and introduced into *E. coli* TG1 by electroporation. After amplification of the plasmid in bacteria, the sequence of the insert was determined.

EXAMPLE 6

Raising Antibodies Against SNEV and Immunofluorescence

For further analyses antibodies against synthetic peptides of SNEV were raised in rabbits and the cellular location of SNEV was determined by immunofluorescent methods.

Determination of Putative Antigenic Sites:

By means of Swiss-model software (http://www.expasy.ch/swissmod/SWISSMODEL.html), a possible tertiary structure of SNEV was predicted for the amino acids 229–421. Using also the PCGENE software three possible antigenic sites were selected and the following peptides were synthesized:

Peptide 86 ($NH_3$-CSWFHPSQDLVFSASPDATI-COOH; SEQ ID NO 5), containing a SNEV sequence of 20 amino acids plus an additional cystein at the N-terminus, including the expected antigenic site at amino acids 276–280, Peptide 87 ($NH_3$—CNVVVFDKSSEQILATLKGHTC-COOH; SEQ ID NO 6) containing a SNEV sequence of 21 amino acids plus an additional cystein at the N-terminus, including the expected antigenic site at amino acids 253–258, and Peptide 88 ($NH_3$—CKATVLTTERKKRGKTVPEELC-COOH; SEQ ID NO 7) containing a SNEV sequence of 21 amino acids plus an additional cystein at the N-terminus, including the expected antigenic site at amino acids 186–192.

The N-terminal cysteine-residue was added to allow for specific coupling to activated keyhole limpet hemocyanin (KLH) using the bifunctional reagent m-maleinimidobenzoyl-N-hydroxysuccinimide ester (MBS).

20 mg KLH were dissolved in 2 ml 0.1 M $Na_2PO_4$ buffer, pH 7.2 and 0.9 M NaCl and mixed with 240 µl of the cross linking reagent MBS (10 mg/ml 0.1 M $NaPO_4$ buffer, pH 7.2, 0.9 M NaCl, and 20% DMSO). Reaction was carried out at room temperature for 2.5 h under constant stirring. Activated KLH was purified by gel exclusion chromatography with a Sephadex G25 column and eluted with 3.5 ml of elution buffer (0.1 M $NaPO_4$ buffer, pH 7.2, 0.9 M NaCl, 0.1 M EDTA). 10 mg of each of the three peptides were dissolved in 1 ml 0.1 M $Na_2PO_4$ buffer, pH 7.2, 0.9 M NaCl, 0.1 M EDTA and 20% DMSO and 600 µl thereof were mixed with 1.15 ml KLH solution. Coupling reaction was carried out overnight at room temperature (RT) under constant stirring.

Peptide conjugates were sterile filtered, mixed one to one with incomplete Freund's adjuvans and injected intramuscularly into New Zealand rabbits. Three immunizations were performed in intervals of three weeks. Blood was collected two weeks after the third immunization.

Indirect Immunofluorescence Using Fluorescence Microscopy:

HaCat cells and normal human diploid fibroblasts were inoculated in an approximate concentration of $5 \times 10^4$ cells/200 µl on cover slips in a 6-well plate and incubated between 24 and 72 h at 37° C. until the cells had reached about 60% confluence. The adhered cells were washed twice with PBS (37° C.), fixed with methanol (−20° C.) for 5 min, air-dried and rinsed with PBS. After blocking with PBS containing 20% FCS (PBS/FCS) for 15 min/RT the cells were incubated with one of the anti-peptide antisera (1:100 in PBS) for 1 h at 37° C. and then washed three times (5 min) with PBS/FCS. Thereafter cells were incubated with a second FITClabeled antibody (light-protected) directed against the first antibody and washed 4 times (10 min) with PBS. The fluorescence signal was visualized using fluorescence microscopy (BioRad MRC600 confocal microscope) with an excitation wavelength of 488 nm and an emission wavelength higher than 515 nm.

The pictures in FIG. 8 show the two cell lines (HaCat and HDF) analyzed for SNEV localization. SNEV was stained by the anti-86 peptide antiserum and found to be localized on the surface of the cell nuclei spreading into the cytoplasm. Wether it is also contained within the nuclei, as suggested by FIG. 8A, has to be determined by further experiments. However, the fluorescence intensity in HaCat cells (A and B) is higher than in HDF (C and D). This result complies with the data obtained from the mRNA analyses (Example 1). Additionally, anti-87 peptide and anti-88 peptide antiserum also stained SNEV (data not shown), which confirms the antigenicity of peptides 87 and 88. Both latter peptides were able to induce anti-SNEV antibodies, the immune response triggered was less pronounced, however, than with peptide 86. The results suggest to use antibodies particularly from the anti-86 peptide antiserum at least as diagnostic tools for the qualitative and quantitative determination of intra- or extracellular levels of SNEV protein, particularly in the course of tumor or cancer diagnostics. Anti-SNEV antibodies may, however, also be applied therapeutically to decrease cellular SNEV protein levels in order to force a targeted cell population, e.g., tumor cells, into early senescence and proliferation stop. For reaching intracellular SNEV proteins, the anti-SNEV antibodies may optionally be modified in a way known in the art such as to be able to enter a target cell from the exterior or to get internalized by any known, e.g., receptor-mediated, endocytosis mechanism.

EXAMPLE 7

Recombinant Expression of SNEV by the Baculo Virus System

In order to produce acceptable amounts of SNEV protein for biochemical studies we recombinantly expressed it by means of the baculo virus insect cell system.

Construction of pBacPAK8-SNEV:

PCR (annealing temperature 50° C.) using Dynazyme EXT (Finnzymes) was performed using the primers SNEV-sense-XbaI (GATGATTCTAGAAATATGTCCCTAATCT-GCTCCAT; SEQ ID NO 12) and SNEV-antisense-StrepTag-EcoRI (GACGGAATTCAACCTAATGATGATGAT-GATGATGCAG GCTGTAGAACTTGAGGC; SEQ ID NO 13). The PCR product was gel-purified and sequentially digested with EcoRI and XbaI. The purified fragment was ligated into EcoRI and XbaI cleaved pBacPAK8 plasmid (Clontech) and transformed into electrocompetent E. coli TG1. A PCR-screening of several transformants was conducted using the vector-specific primers −44back (TTTACT-GTTTTCGTAACAGTTTTG; SEQ ID NO 14) and +1660 for (CAACGCACAGAATCTAGCGC; SEQ ID NO 15). Plasmid-DNA from three putative candidates was extracted (GFX-Kit, Pharmacia), verified by restriction-analysis and designated pBacPAK8-SNEV.

Cell Culture and Virus Propagation:

Sf9 insect cells (*Spodoptera frugiperda*, ATCC CRL 117) were grown in IPL-41 medium (Sigma) supplemented with 3% fetal calf serum (FCS), and with 10% FCS when used for virus propagation.

Construction of Recombinant Baculovirus Particles AcSNEV:

50 ng pBacPAK8-SNEV DNA were complexed using Cellfectin (LTI) and co-transfected with 250 ng BaculoGold DNA (Pharmingen) into $2,5 \times 10^6$ Sf9 cells. After three days a plaque-assay with the transfection supernatant was performed and incubated for seven days. Twelve individual plaques were transferred onto fresh Sf9 cells (24 well plate) and amplified for five days. Infected cells were harvested and baculoviral DNA was extracted from the pellets following the standard protocol for alkaline lysis. After PCR-screening with the primer pair −44 back and +1660 for three positive clones were amplified in T25-flasks (IPL-41, 10% FCS): $2,5 \times 10^6$ Sf9 cells were infected with 50 µl supernatant and amplified for three days. AcSNEV intermediate stock was harvested via centrifugation and stored at 4° C.

Expression of SNEV with Recombinant Baculovirus AcSNEV:

$8 \times 10^6$ µg cells were seeded in a T80-flask and infected with 50 µl AcSNEV intermediate stock. A second flask was infected with AcΩ, a polyhedrin-negative baculoviral construct with no recombinant gene, which served as a negative control. Infected cells were harvested 48 hours after infection and lysed with single detergent buffer (50 mM TRIS/HCl pH 8,0; 150 mM NaCl 100 µg/ml PMSF; 1% Triton X-100; Aprotinin).

SDS-PAGE Electrophoresis and Western Blots:

The cell lysate was centrifuged at maximum speed for 10 min/RT and the clear supernatant was transferred to a fresh microcentrifuge tube. 10 µl of cell lysate were mixed with 10 µl 2×SDS gel loading buffer, boiled for 10 min and separated by SDS-PAGE on 10% polyacrylamide gels with 5% stacking gels. Gels were run in 1× Laemmli buffer (25 mM Tris/HCl pH 8.6; 192 mM Glycine; 0.1% SDS) for 1 h at 180 V. Proteins contained in the gels were detected by silver stain (FIG. 9A) or by Western blots (FIG. 9B).

Gel membrane and filter papers were incubated for 10 min in transfer buffer (25 mM Tris base; 150 mM glycine; 10% methanol), then semi-dry electrotransfer of proteins to nitrocellulose membranes was performed for 1 h at 10 V with transfer buffer. Membranes were washed twice for 10 min/RT in TBS-buffer (10 mM Tris/HCl pH 7.5; 150 mM NaCl) and blocked using Western blot blocking solution (10 mM Tris/HCl pH 7.5; 150 mM NaCl; 3% BSA) for 1 h/RT. Membranes were washed twice for 10 min/RT in TBS-buffer and were incubated with a dilution of anti-86 antibody in Western blot blocking solution (1/100). After washing twice with TBS buffer for 10 min/RT, membranes were incubated with the secondary antibody (mouse anti rabbit conjugated with horse radish peroxidase, Sigma) for 1 h/RT. After washing 4 times with TBS buffer 10 min/RT, detection was carried out using the ECL plus kit (Amersham Pharmacia Biotech) according to the manufacturer's guidelines.

As shown in FIG. 9, recombinant SNEV protein was expressed as a strep-tag fusion protein in a soluble form by insect cells. It was detected in the insect cell lysate after removing cell debris by centrifugation (FIG. 9B, lane 3). Thus a method to produce high amounts of recombinant SNEV has been established and purification by means of a streptactin affinity column is performed.

Abbreviations:

| | |
|---|---|
| aa | amino acids |
| DIG | digoxigenin |
| EST | expressed sequence tag |
| G418 | antibiotic against eukaryotic cells |
| G3PDH | glycerol-3-phosphate dehydrogenase |
| hTERT | human telomerase |

-continued

| | |
|---|---|
| HUVEC | human umbilical vein endothelial cell |
| KLH | keyhole limpet hemocyanine |
| MBS | m-maleinimidobenzoyl-N-hydroxysuccinimide ester |
| PAC | P1-derived artificial chromosome |
| PNA | peptide nucleic acid |
| SNEV | artificial name of instant protein (SEQ ID NO 2) |

What is claimed is:

1. An isolated or synthetically produced nucleotide sequence encoding a cell regulatory protein having the amino acid sequence of SEQ ID NO: 4 or comprising a part SEQ ID NO: 4, wherein:
   the part of SEQ ID NO: 4 is selected from the group consisting of peptide 86 (SEQ ID NO: 5), peptide 87 (SEQ ID NO: 6), and peptide 88 (SEQ ID NO: 7).

2. The nucleotide sequence according to claim 1, comprising SEQ ID NO: 3.

3. An isolated or synthetically produced sense mRNA that translates into a cell regulatory protein having the amino acid sequence of SEQ ID NO: 4, or comprising a part of SEQ ID NO: 4, wherein
   the part of SEQ ID NO: 4 is selected from the group consisting of peptide 86 (SEQ ID NO: 5), peptide 87 (SEQ ID NO: 6), and peptide 88 (SEQ ID NO: 7).

4. A method for prolonging the life span of a eukaryotic cell, comprising:
   transfecting sense mRNA that translates into a cell regulatory protein into the eukaryotic cell and incubating the cell in a suitable cell culture medium, the cell regulatory protein having an amino acid sequence of SEQ ID NO: 4comprising a part of SEQ ID NO: 4, the part of SEQ ID NO: 4.

* * * * *

SEQUENCE LISTING

<160> NUMBER OF SEQ ID NOS: 15

<210> SEQ ID NO 1
<211> LENGTH: 1883
<212> TYPE: DNA
<213> ORGANISM: Mus sp.
<220> FEATURE:
<223> OTHER INFORMATION: Sequence from murine cell line 3T3; putative
      coding sequence of mSNEV protein (504 amino acids)
      starts at bp 185

<400> SEQUENCE: 1

```
aaggctgagg cgcgccaccg gcacctcccc acgtgaagca gttgtgcgag catcgcacgc      60
tgggcagctg tctacccgcg tccgagcgct ccggaagcgg cggggaccg gaagtggccc     120
gcggaggatg cagagaaccg ggaaccctct gtgaggcgac tggcagcagc gctacgacgg     180
cgccatgtcc ctgatctgct cgatctccaa tgaagtgcca gagcacccgt gcgtgtcccc     240
tgtctctaat catgtgtatg agcggcgact cattgagaag tacattgcag agaatggcac     300
agatcctatc aacaaccagc ctctctcaga ggagcagctc atcgacatca agttgctca      360
cccaatccga cccaagcctc cctccgccac cagcatccca gccattctga agccttgca      420
ggatgagtgg gatgcagtca tgctgcacag cttcactctt cgccagcaac tgcagacaac      480
ccgccaggag ctgtcccatg ctctgtacca acacgatgct gcctgccgag tcattgcccg      540
gctcaccaaa gaggtcactg ctgctcgaga agctctggct actctgaaac acaggctgg      600
gcttattgta cctcaggctg tgccaagctc acagcccagt gttgtgggtg caggagagcc      660
catggatttg ggtgagctgg tgggaatgac ccctgagatt atccagaagc ttcaagacaa      720
ggctactgtg ctaaccacgg agcgtaagaa gagaggaaag actgtccccg aggagctggt      780
gaaacctgaa gagctcagca agtaccggca ggtggcatcc catgtgggtc tacacagtgc      840
tagcattcct gggattctcg ctctggacct gtgtccctca gacaccaaca agattctcac      900
tggtggggca gataaaaatg ttgttgtctt tgataagagt actgagcaaa tattggccac      960
tctcaaaggc cataccaaga aggtcaccag tgtggtgttt catccttctc aggaactggt     1020
gttttctgcg tccctgatg ctactatcag gatttggtca gtcccgaaca cttcctgcgt     1080
acaggttgtt cgggcccatg agagtgcagt gacaggcctc agcctccatg ctactggaga     1140
ctatctcctg agctcctctg atgatcagta ctgggccttc tctgacatcc agacaggcg      1200
tgtgctcact aaggtgacag atgagacctc cggctgctct cttacctgtg cacagttcca     1260
ccctgatggg ctcatctttg gaacaggaac catggactcc cagatcaaga tctgggactt     1320
gaaggagcgt accaatgtgg ccaacttccc tggccattct ggcccatta ccagcatcgc     1380
cttctctgag aatgggtact acctggccac agcagctgat gattcctcag tcaagctctg     1440
```

```
ggacttacgc aagttgaaga acttcaagac attgcagctg acaacaact ttgaggtgaa    1500 gtcactaatc tttgaccaga gcggtaccta cctggcgctt gggggtacag atgtccagat    1560
ctacatctgc aaacaatgga cagagattct tcactttaca gagcacagtg gcctgaccac    1620
tggagtggcc tttggacacc atgccaagtt catcgcttca actggcatgg acaggagcct    1680
caaattctac agtctgtagg ccctatgcct tctcacagtt ctgggcctca tctcagtagt    1740
gggttagagt tagagggtgg gggtgggggt gggactttag gaggagaggg aggtctggtt    1800
ggggggggac attcacatca tttcattttg gtctggatga tggtctgagc cagggcacat    1860
agaacattgc tatccatgca gcc                                             1883
```

<210> SEQ ID NO 2
<211> LENGTH: 504
<212> TYPE: PRT
<213> ORGANISM: Mus sp.
<220> FEATURE:
<223> OTHER INFORMATION: Amino acid sequence corresponding to nucleotide sequence of SEQ ID NO.1

<400> SEQUENCE: 2

```
Met Ser Leu Ile Cys Ser Ile Ser Asn Glu Val Pro Glu His Pro Cys
1               5                   10                  15

Val Ser Pro Val Ser Asn His Val Tyr Glu Arg Arg Leu Ile Glu Lys
            20                  25                  30

Tyr Ile Ala Glu Asn Gly Thr Asp Pro Ile Asn Asn Gln Pro Leu Ser
        35                  40                  45

Glu Glu Gln Leu Ile Asp Ile Lys Val Ala His Pro Ile Arg Pro Lys
    50                  55                  60

Pro Pro Ser Ala Thr Ser Ile Pro Ala Ile Leu Lys Ala Leu Gln Asp
65                  70                  75                  80

Glu Trp Asp Ala Val Met Leu His Ser Phe Thr Leu Arg Gln Gln Leu
                85                  90                  95

Gln Thr Thr Arg Gln Glu Leu Ser His Ala Leu Tyr Gln His Asp Ala
            100                 105                 110

Ala Cys Arg Val Ile Ala Arg Leu Thr Lys Glu Val Thr Ala Ala Arg
        115                 120                 125

Glu Ala Leu Ala Thr Leu Lys Pro Gln Ala Gly Leu Ile Val Pro Gln
    130                 135                 140

Ala Val Pro Ser Ser Gln Pro Ser Val Val Gly Ala Gly Glu Pro Met
145                 150                 155                 160

Asp Leu Gly Glu Leu Val Gly Met Thr Pro Glu Ile Ile Gln Lys Leu
                165                 170                 175

Gln Asp Lys Ala Thr Val Leu Thr Thr Glu Arg Lys Lys Arg Gly Lys
            180                 185                 190

Thr Val Pro Glu Glu Leu Val Lys Pro Glu Glu Leu Ser Lys Tyr Arg
        195                 200                 205

Gln Val Ala Ser His Val Gly Leu His Ser Ala Ser Ile Pro Gly Ile
    210                 215                 220

Leu Ala Leu Asp Leu Cys Pro Ser Asp Thr Asn Lys Ile Leu Thr Gly
225                 230                 235                 240

Gly Ala Asp Lys Asn Val Val Phe Asp Lys Ser Thr Glu Gln Ile
                245                 250                 255

Leu Ala Thr Leu Lys Gly His Thr Lys Lys Val Thr Ser Val Val Phe
            260                 265                 270
```

-continued

```
His Pro Ser Gln Glu Leu Val Phe Ser Ala Ser Pro Asp Ala Thr Ile
        275                 280                 285
Arg Ile Trp Ser Val Pro Asn Thr Ser Cys Val Gln Val Val Arg Ala
        290                 295                 300
His Glu Ser Ala Val Thr Gly Leu Ser Leu His Ala Thr Gly Asp Tyr
305                 310                 315                 320
Leu Leu Ser Ser Asp Asp Gln Tyr Trp Ala Phe Ser Asp Ile Gln
                325                 330                 335
Thr Gly Arg Val Leu Thr Lys Val Thr Asp Glu Thr Ser Gly Cys Ser
            340                 345                 350
Leu Thr Cys Ala Gln Phe His Pro Asp Gly Leu Ile Phe Gly Thr Gly
            355                 360                 365
Thr Met Asp Ser Gln Ile Lys Ile Trp Asp Leu Lys Glu Arg Thr Asn
370                 375                 380
Val Ala Asn Phe Pro Gly His Ser Gly Pro Ile Thr Ser Ile Ala Phe
385                 390                 395                 400
Ser Glu Asn Gly Tyr Tyr Leu Ala Thr Ala Ala Asp Asp Ser Ser Val
                405                 410                 415
Lys Leu Trp Asp Leu Arg Lys Leu Lys Asn Phe Lys Thr Leu Gln Leu
            420                 425                 430
Asp Asn Asn Phe Glu Val Lys Ser Leu Ile Phe Asp Gln Ser Gly Thr
            435                 440                 445
Tyr Leu Ala Leu Gly Gly Thr Asp Val Gln Ile Tyr Ile Cys Lys Gln
        450                 455                 460
Trp Thr Glu Ile Leu His Phe Thr Glu His Ser Gly Leu Thr Thr Gly
465                 470                 475                 480
Val Ala Phe Gly His His Ala Lys Phe Ile Ala Ser Thr Gly Met Asp
                485                 490                 495
Arg Ser Leu Lys Phe Tyr Ser Leu
            500
```

<210> SEQ ID NO 3
<211> LENGTH: 2216
<212> TYPE: DNA
<213> ORGANISM: Homo sapiens
<220> FEATURE:
<223> OTHER INFORMATION: Sequence obtained from human umbilical vein
endothelial cell;  putative coding sequence of
SNEV protein (504 amino acids) starts at bp 91

<400> SEQUENCE: 3

```
cagcagcggg ggaccggaag tggctcgcgg aggctcagaa gctagtcccg gagcccggcg    60
tgtggcgcct cggagcgcgg tgacggcgcc atgtccctaa tctgctccat ctctaacgaa   120
gtgccggagc acccatgtgt atccctgtc tctaatcatg tttatgagcg gcggctcatc   180
gagaagtaca ttgcggagaa tggtaccgac cccatcaaca accagcctct ctccgaggag   240
cagctcatcg acatcaaagt tgctcaccca atccggccca gcctccctc agccaccagc   300
atcccggcca ttctgaaagc tttgcaggat gagtgggatg cagtcatgct gcacagcttc   360
actctgcgcc agcagctgca gacaacccgc caagagctgt cacacgctct gtaccagcac   420
gatgccgcct gccgtgtcat tgcccgtctc accaaggaag tcactgctgc ccgagaagct   480
ctggctaccc tgaaaccaca ggctggcctc attgtgcccc aggctgtgcc aagttcccaa   540
ccaagtgttg tgggtgcggg tgagccaatg gatttgggtg agctggtggg aatgacccca   600
gagattattc agaagcttca agacaaagcc actgtgctaa ccacgagcg caagaagaga   660
```

-continued

```
gggaagactg tgcctgagga gctggtgaag ccagaagagc tcagcaaata ccggcaggtg      720
gcatcccacg tggggttgca cagtgccagc attcctggga tcctggccct ggacctctgc      780
ccgtccgaca ccaacaagat cctcactggt ggggcggata aaatgtcgt tgtgtttgac       840 aaaagttctg aacaaatcct ggctaccctc aaaggccata ccaagaaggt caccagcgtg      900
gtgtttcacc cttcccagga cctggtgttt tctgcttccc ccgatgccac tatcaggatt     960
tggtcggtcc ccaatgcctc ttgtgtacag gtggttcggg cccatgagag tgctgtgaca    1020
ggcctcagcc ttcatgccac tggcgactat ctcctgagct cctccgatga tcagtactgg    1080
gctttctctg acatccagac agggcgtgtg ctcaccaagg tgacagatga acctccggc     1140 tgctctctca cctgtgcaca gttccaccct gacggactca tctttggaac aggaaccatg    1200
gactctcaga tcaagatctg ggacttgaag gaacgtacta atgtggccaa cttccctggc    1260
cactcgggcc ccatcactag catcgccttc tctgagaatg gttactacct ggctacagcg    1320
gctgatgact cctctgtcaa gctctgggat ctgcgcaagc ttaagaactt taagactttg    1380
cagctggata caactttga ggtaaagtca ctgatctttg accagagtgg tacctacctg    1440
gctcttgggg gcacggatgt ccagatctac atctgcaaac aatggacgga gattcttcac    1500
tttacagagc atagcggcct gaccacaggg gtggccttcg gcatcacgc caagttcatc     1560 gcttcaacag gcatggacag aagcctcaag ttctacagcc tgtaggccct ggcccttctg    1620
atggaagctg ggcctcatct cagtagaggg gtagaattag ggtttggggg gggggtgggg   1680
ggaatctatg ggggagggg gctctgtggg gtgggacatt cacatcattt cactctggtc    1740
tgagtggtgg cctgagaacc atggtggcat ggaccaccct catccatgca actccaggcc    1800
ccatgggaac ggatgtggaa ggaagaactg tcaccctctt aaggcccagg gtcggagccc    1860
agggcctctc ccttcctgtc gttcaatgga cgtggtggtg gctgttccac acccattttg    1920
ttgcagttcc tgtgagacag gagaggctga gccaagggaa ctgtgaaggg gatgggcagg    1980
agggcttgtg cagggttttg taagcagtga tctagtttca ttaaaaaaag aaaacaataa    2040
ccataaccac ctcccccgtgt ctgtctgcac caggagcacc tgggactggg aaggtcaagg    2100
ggagggagca cacactggga cactggcttc cgggaagccc atcttccttt cctttcacag    2160 ctcttacccct tttttttttt ttttttaattg cacagcagaa ataaaaacaa atctgc        2216
```

<210> SEQ ID NO 4
<211> LENGTH: 504
<212> TYPE: PRT
<213> ORGANISM: Homo sapiens
<220> FEATURE:
<223> OTHER INFORMATION: Amino acid sequence corresponding to nucleotide
      sequence of SEQ ID NO.3

<400> SEQUENCE: 4

```
Met Ser Leu Ile Cys Ser Ile Ser Asn Glu Val Pro Glu His Pro Cys
1               5                  10                  15

Val Ser Pro Val Ser Asn His Val Tyr Glu Arg Arg Leu Ile Glu Lys
            20                  25                  30

Tyr Ile Ala Glu Asn Gly Thr Asp Pro Ile Asn Asn Gln Pro Leu Ser
        35                  40                  45

Glu Glu Gln Leu Ile Asp Ile Lys Val Ala His Pro Ile Arg Pro Lys
    50                  55                  60

Pro Pro Ser Ala Thr Ser Ile Pro Ala Ile Leu Lys Ala Leu Gln Asp
65                  70                  75                  80

Glu Trp Asp Ala Val Met Leu His Ser Phe Thr Leu Arg Gln Gln Leu
```

-continued

```
                 85                  90                  95
Gln Thr Thr Arg Gln Glu Leu Ser His Ala Leu Tyr Gln His Asp Ala
            100                 105                 110
Ala Cys Arg Val Ile Ala Arg Leu Thr Lys Glu Val Thr Ala Ala Arg
            115                 120                 125
Glu Ala Leu Ala Thr Leu Lys Pro Gln Ala Gly Leu Ile Val Pro Gln
            130                 135                 140
Ala Val Pro Ser Ser Gln Pro Ser Val Val Gly Ala Gly Glu Pro Met
145                 150                 155                 160
Asp Leu Gly Glu Leu Val Gly Met Thr Pro Glu Ile Ile Gln Lys Leu
            165                 170                 175
Gln Asp Lys Ala Thr Val Leu Thr Thr Glu Arg Lys Lys Arg Gly Lys
            180                 185                 190
Thr Val Pro Glu Glu Leu Val Lys Pro Glu Glu Leu Ser Lys Tyr Arg
            195                 200                 205
Gln Val Ala Ser His Val Gly Leu His Ser Ala Ser Ile Pro Gly Ile
            210                 215                 220
Leu Ala Leu Asp Leu Cys Pro Ser Asp Thr Asn Lys Ile Leu Thr Gly
225                 230                 235                 240
Gly Ala Asp Lys Asn Val Val Phe Asp Lys Ser Ser Glu Gln Ile
            245                 250                 255
Leu Ala Thr Leu Lys Gly His Thr Lys Lys Val Thr Ser Val Val Phe
            260                 265                 270
His Pro Ser Gln Asp Leu Val Phe Ser Ala Ser Pro Asp Ala Thr Ile
            275                 280                 285
Arg Ile Trp Ser Val Pro Asn Ala Ser Cys Val Gln Val Val Arg Ala
            290                 295                 300
His Glu Ser Ala Val Thr Gly Leu Ser Leu His Ala Thr Gly Asp Tyr
305                 310                 315                 320
Leu Leu Ser Ser Ser Asp Asp Gln Tyr Trp Ala Phe Ser Asp Ile Gln
            325                 330                 335
Thr Gly Arg Val Leu Thr Lys Val Thr Asp Glu Thr Ser Gly Cys Ser
            340                 345                 350
Leu Thr Cys Ala Gln Phe His Pro Asp Gly Leu Ile Phe Gly Thr Gly
            355                 360                 365
Thr Met Asp Ser Gln Ile Lys Ile Trp Asp Leu Lys Glu Arg Thr Asn
            370                 375                 380
Val Ala Asn Phe Pro Gly His Ser Gly Pro Ile Thr Ser Ile Ala Phe
385                 390                 395                 400
Ser Glu Asn Gly Tyr Tyr Leu Ala Thr Ala Ala Asp Asp Ser Ser Val
            405                 410                 415
Lys Leu Trp Asp Leu Arg Lys Leu Lys Asn Phe Lys Thr Leu Gln Leu
            420                 425                 430
Asp Asn Asn Phe Glu Val Lys Ser Leu Ile Phe Asp Gln Ser Gly Thr
            435                 440                 445
Tyr Leu Ala Leu Gly Gly Thr Asp Val Gln Ile Tyr Ile Cys Lys Gln
            450                 455                 460
Trp Thr Glu Ile Leu His Phe Thr Glu His Ser Gly Leu Thr Thr Gly
465                 470                 475                 480
Val Ala Phe Gly His His Ala Lys Phe Ile Ala Ser Thr Gly Met Asp
            485                 490                 495
Arg Ser Leu Lys Phe Tyr Ser Leu
            500
```

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: part of
    peptide chain of SNEV-protein (SEQ ID NO 4)
    containing antigenic site

<400> SEQUENCE: 5

Cys Ser Val Val Phe His Pro Ser Gln Asp Leu Val Phe Ser Ala Ser
1               5                   10                  15

Pro Asp Ala Thr Ile
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: part of peptide chain of SNEV protein (SEQ ID NO 4) containing antigenic site

<400> SEQUENCE: 6

```
Cys Asn Val Val Val Phe Asp Lys Ser Ser Glu Gln Ile Leu Ala Thr
1               5                   10                  15

Leu Lys Gly His Thr Cys
            20
```

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: part of peptide chain of SNEV protein (SEQ ID NO 4) containing antigenic site

<400> SEQUENCE: 7

```
Cys Lys Ala Thr Val Leu Thr Thr Glu Arg Lys Lys Arg Gly Lys Thr
1               5                   10                  15

Val Pro Glu Glu Leu Cys
            20
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: retro SNEV sense primer

<400> SEQUENCE: 8

```
gacggttaac atgtccctaa tctgctccat                                        30
```

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: retro SNEV antisense primer

<400> SEQUENCE: 9
gaccgttaac cctaattcta cccctctac                                    29

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: mSNEV sense
      primer

<400> SEQUENCE: 10
aaccctctgt gaggcgactg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: mSNEV
      antisense primer

<400> SEQUENCE: 11
ccactactga gatgaggccc                                              20

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: SNEV sense
      XbaI primer

<400> SEQUENCE: 12
gatgattcta gaaatatgtc cctaatctgc tccat                             35

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence: SNEV
      antisense StrepTag EcoRI primer

<400> SEQUENCE: 13
gacggaattc aacctaatga tgatgatgat gatgcaggct gtagaacttg aggc         54

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      vector-specific primer -44back

<400> SEQUENCE: 14
tttactgttt tcgtaacagt tttg                                         24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      vector-specific primer +1660for

```
<400> SEQUENCE: 15
caacgcacag aatctagcgc                                                              20
```